US00PP22570P2

(12) United States Plant Patent
Bock

(10) Patent No.: US PP22,570 P2
(45) Date of Patent: Mar. 13, 2012

(54) HYBRID RUGOSA ROSE PLANT NAMED 'BOC ROGOSNIF'

(50) Latin Name: ***Rosa* hybrid**
Varietal Denomination: BOC rogosnif

(76) Inventor: Charles Wendell Bock, Burnsville, MN (US)

( * ) Notice: Subject to any disclaimer, the term of this patent is extended or adjusted under 35 U.S.C. 154(b) by 50 days.

(21) Appl. No.: 12/800,996

(22) Filed: May 27, 2010

(51) Int. Cl.
*A01H 5/00* (2006.01)

(52) U.S. Cl. ..... Plt./102

(58) Field of Classification Search ..... Plt./102
See application file for complete search history.

(56) References Cited

OTHER PUBLICATIONS

Kelli Rodda, Introductions, Nursery Management & Production Magazine, Jun. 2009, P-6, vol. 25, No. 6, GIE Media Inc., Richfield, OH USA.

Chuck & Char Bock, Trial Ground Winner: Amateur Hybridizer Wins The Gold, American Rose Magazine, Jul./Aug. 2009, p. 56-58, vol. XXXX, N-4 American Rose Society, Shreveport LA USA.

*Primary Examiner* — Kent L Bell

(57) ABSTRACT

A new cultivar of Hybrid Rugosa rose, *Rosa* 'BOC rogosnif', characterized by its clusters of semi-double, cupped shaped blooms of beetroot purple suffused magenta color, white streaked eye, gold stamens, strong, cinnamon fragrance, dark green, glossy foliage, resistance to major fungal diseases, vigorous, upright, bushy habit, continuous flowering, readily propagated via budding or rooted cuttings, and hardy in U.S.D.A. Zones 3-10.

2 Drawing Sheets

Botanical designation: *Rosa* hybrid.
Cultivar denomination: 'BOC rogosnif'.

BACKGROUND OF THE INVENTION

The present invention relates to a new and distinct cultivar of *Rosa hybrida*. The new cultivar will be referred to hereafter by its cultivar name, 'BOC rogosnif'. 'BOC rogosnif' is a Hybrid Rugosa rose suitable for use in the commercial market class of shrub roses, eco-friendly for residential gardens, mixed flower plantings, and commercial landscaping.

The new cultivar of shrub rose is a selection from a controlled and planned breeding program conducted in 1995, by the inventor located in Burnsville, Minn., U.S.A. The breeding was established to create roses with greater winter hardiness, novel flower colors, continuous flowering without deadheading, very strong fragrance, complete disease resistance, and maintenance free.

The inventor created a new cultivar of Hybrid Rugosa rose 'BOC rogosnif' designated as seedling No. CB-9505. From a planned breeding program, the cultivar was selected among seedlings derived from a cross made in Burnsville, Minn., U.S.A., in 1995. The cross was made between a Hybrid Rugosa seedling of the inventor's 'BOC germ' as the female parent and a miniature rose seedling of the inventor 'BOC eye' as the male parent. In 1997, the inventor identified 'BOC rogosnif' as a novel rose cultivar.

Asexual reproduction of 'BOC rogosnif' was performed by rooting softwood and semi-hardwood cuttings and budding from the original plant of 'BOC rogosnif' from 1997 to 1998 in Burnsville, Minn., U.S.A. The reproduction established and transmitted all the characteristics and distinctions claimed through succeeding propagations. The characteristics of this cultivar are stable and are reproduced true to type in successive generations.

SUMMARY OF THE INVENTION

The following traits have been repeatedly observed and represent the characteristics of the new rose as observed for a period of 12 years in Burnsville, Minn., U.S.A. and 2 years of testing under contract at American Rose Society trial grounds in Shreveport, La., U.S.A. These attributes in combination distinguish 'BOC rogosnif' as a unique cultivar of rose, and distinguish it from its parents, as well as all other varieties of which I am aware. 1. 'BOC rogosnif' exhibits clusters of very fragrant cinnamon-scented, cupped, semi-double flowers of novel beetroot purple color, suffused with bright magenta as they mature, white streaked eye, prominent gold stamens. 2. 'BOC rogosnif' is classified as mauve and mauve blend by American Rose Society Standards. 3. 'BOC rogosnif' exhibits glossy, dark green foliage that compliments the blooms and plant. 4. 'BOC rogosnif' exhibits an upright, bushy habit with a height of 120 cm. 5. 'BOC rogosnif' exhibits a continuous seasonal flowering habit, without deadheading. 6. 'BOC rogosnif' has shown excellent resistance to major fungal diseases. 7. 'BOC rogosnif' is hardy in U.S.D.A. Zones 3 to 10. 8. 'BOC rogosnif' has the ability to root and grow vigorously when budded, or by softwood and semi-hardwood cuttings.

The new cultivar of shrub rose can be readily distinguished from its parents and other cultivars. The female parent 'BOC germ' is a Hybrid Rugosa seedling of the inventor, never released for sale, with fragrant double pink flowers and green, glossy, rugose foliage, disease resistant, winter hardy. The male parent 'BOC eye' is a miniature rose seedling of the inventor, never released for sale that is not winter hardy and has small, red and white striped flowers and small glossy, green foliage and is disease resistant. The Floribunda rose cultivar 'News' (not patented), and the Hybrid Tea rose cultivar 'Stephens Big Purple' (U.S. Plant Pat. No. 6,262) are close comparison roses. Both cultivars have similarity to 'BOC rogosnif' in having beetroot purple colored flowers, per The Royal National Rose Society (London) color classification. 'BOC rogosnif' and 'News' also exhibit prominent gold stamens. 'BOC rogosnif' is winter hardy in U.S.D.A Zone 3, while 'News' and 'Stephens Big Purple' are U.S.D.A. hardy in Zone 5. The rose variety with the greatest similarity to 'BOC rogosnif' is 'Harvest Home', Hybrid Rugosa (not patented). Both have identical plant habit, but 'Harvest Home' has a mauve-pink flower, slight fragrance, light green foliage, and poor repeat flowering.

The new cultivar, 'BOC rogosnif' will be marketed in the United States under the "SNIFFER" trademark.

BRIEF DESCRIPTION OF THE DRAWINGS

The accompanying colored photographs illustrate the overall appearance and distinct characteristics of the new Hybrid Rugosa rose 'BOC rogosnif', as grown outdoors in trial blocks and mixed flower beds in Burnsville, Minn., U.S.A. The photographs were taken of 3-year-old plants grown on their own roots.

DETAILED BOTANICAL DESCRIPTION

Figure 1:
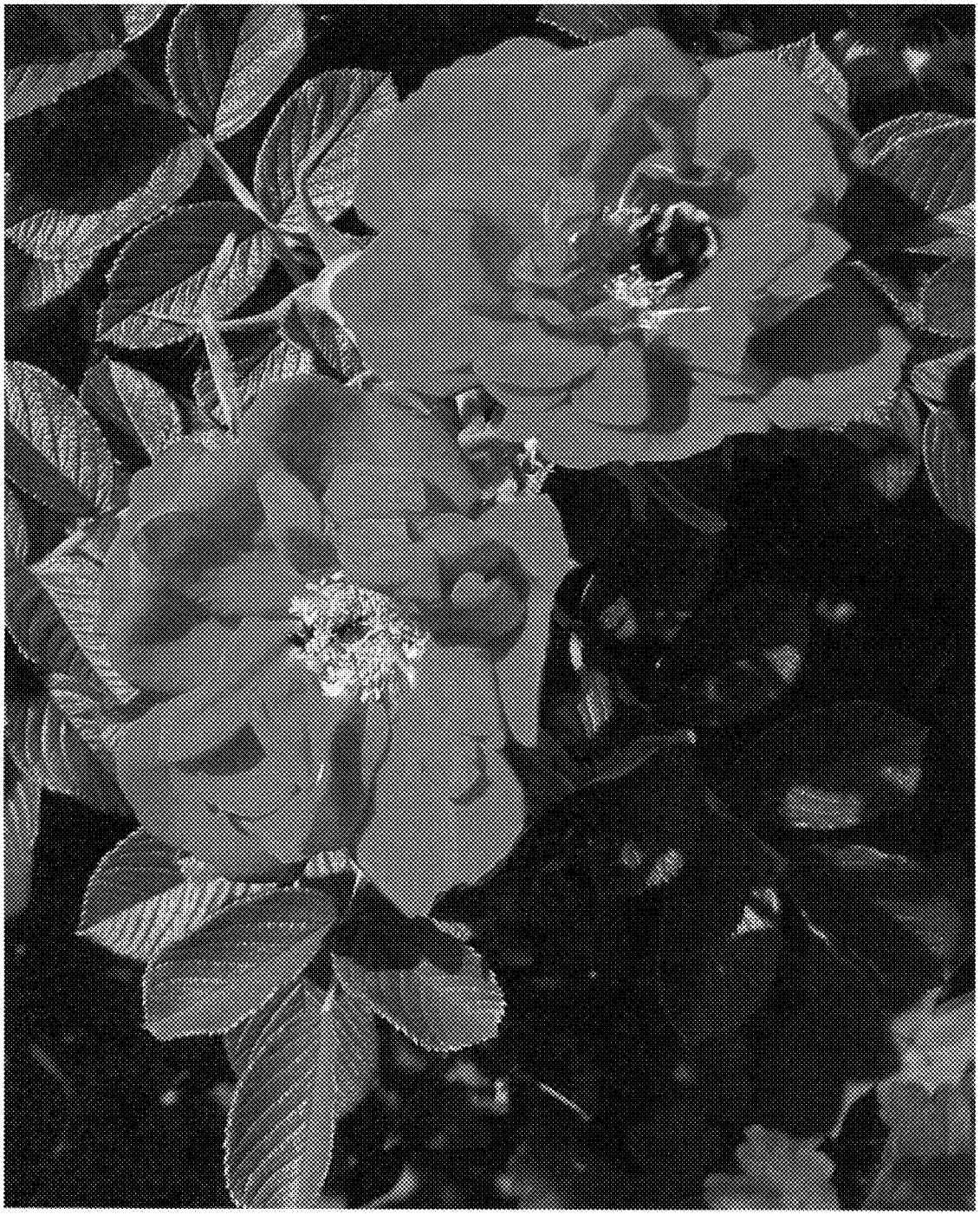
FIG. 1 provides a close-up view of fully open flower clusters.
Figure 2:
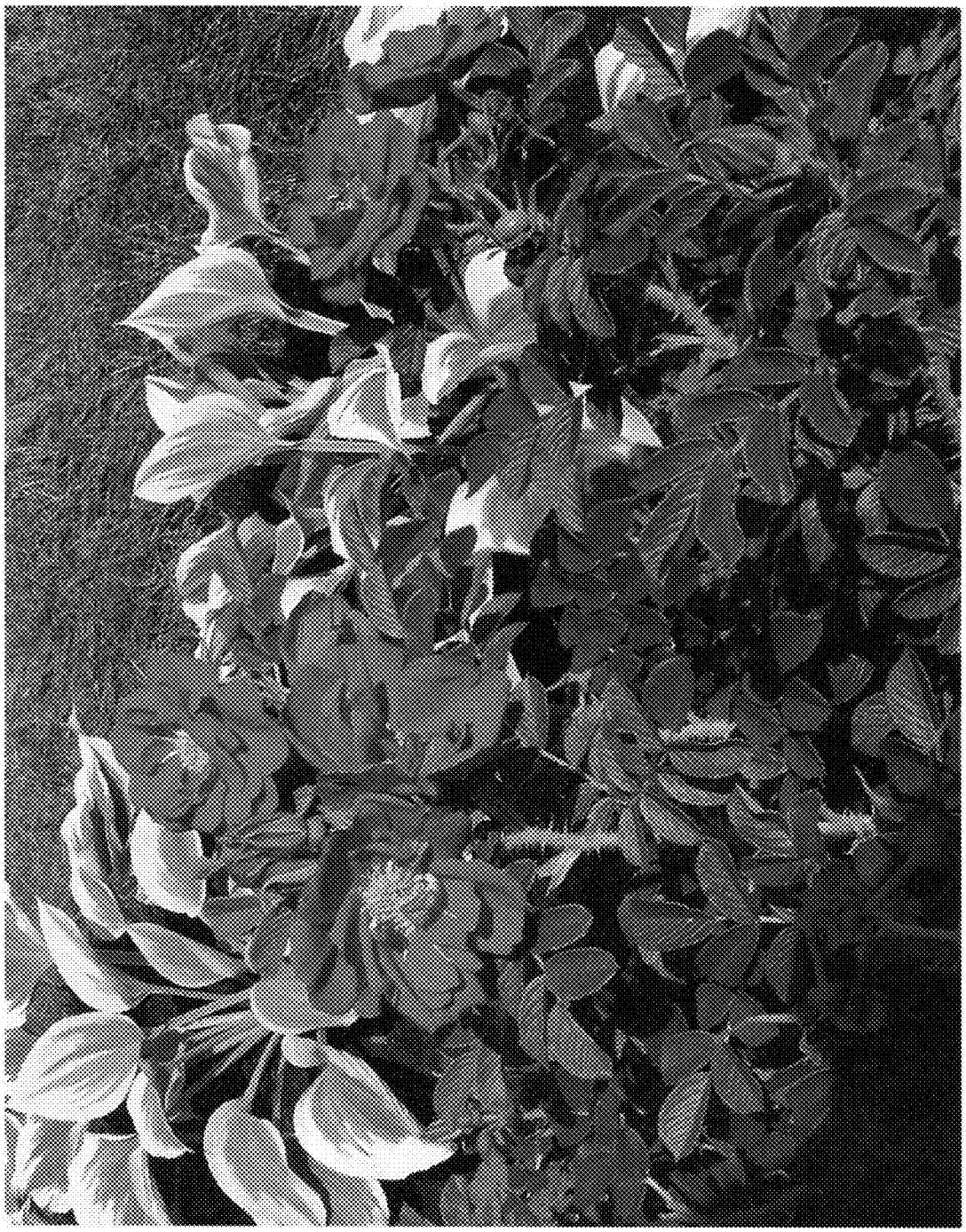
FIG. 2 provides a close-up view of all stages of flower bloom, hip formation, vegetative growth, and foliage.

The following is a detailed description of my new rose cultivar with color descriptions using terminology in accordance with The Royal Horticultural Society (London) Colour Chart (2001), except where ordinary dictionary significance of color is indicated. The phenotype of the new cultivar may vary with variations in environmental, climatic, and cultural conditions, as it has not been tested under all possible environmental conditions. The description is based on observations of plant cuttings and are not grafted onto rootstock.

Parentage:

*Seed parent*.—'BOC germ' a hybrid rugosa seedling of the inventor (not patented).

*Pollen parent*.—'BOC eye' a miniature rose seedling of the inventor (not patented).

Classification:

*Botanical*.—*Rosa* hybrid.

*Commercial market*.—Shrub.

*Class*.—Hybrid Rugosa. Observations were made of plants 2-6 years of age propagated from cuttings and grown in tended gardens located in Burnsville, Minn., U.S.A. and Shreveport, La., U.S.A.

Flower:

*Blooming habit*.—Continuous (U.S.D.A. Zone 4: late May until late October) and reblooms without deadheading spent bloom. Inflorescence Description: Type: Clusters of cupped-shaped flowers. Longevity: 4 to 5 days on the plant depending on temperature and sunlight exposure, 3 days as a cut flower. Fragrance: Very strong, cinnamon scent. Petalage: Typically under normal conditions 9-16 petals. Size: 10 cm in diameter. Borne: Flowers are borne in regular, rounded clusters of 4-6 per stem. Stems: Strong, average length 36-46 cm, diameter 3-10 mm, internode length an average of 2.5 cm. Form: Cupped when blooms first open. Permanence: Blooms retain their form to the end.

*Peduncle*.—Length: Short 25-27 mm. Diameter: 3-4 mm. Surface: Hairy. Color: Yellow-Green Group 147D. Strength: Stiff and erect.

*Bud*.—Size: Average of 3.3 cm in length and 2.6 cm width when the petals start to unfurl. Form: The bud form is long, pointed, and ovoid. Color: When sepals first divide, bud color is Red-Purple Group N57B. When half blown, the upper and lower sides of the petals are a blend of Purple Group N78A and Red-Purple Group N74A; texture is glabrous.

*Sepals*.—There are five unappendaged sepals. Color: Upper surface: Green Group 138B. Lower surface: Green Group 138B. Surface texture: Covered in fine hairs. Length: 25-30 mm. Width: 6-7 mm. Shape: Ovate to oblong. Apex: Acuminate serrated tips.

*Receptacle*.—Color: Green Group 138B. Shape: Elliptic. Size: Medium about 10 mm wide and 11 mm long. Surface: Smooth.

*Petals*.—Color: When opening: Upper surface of petals are Purple Group N78A and Red-Purple Group N74A. The lower surface of petals is Purple Group N78B and Purple Group N78C. The base of each petal has a distinct White Group 155B petal spot on the upper and lower surface which streaks up the petal for about 1 cm. Color: Fully open: Upper surface of petals is Red-Purple Group N74A suffused with Red-Purple Group 67B; lower surface of petals is Red-Purple Group N74B. Variegation: There are occasional white streaks on petal surfaces, White Group 155B. Discoloration: No change in general tonality at the end of the first day. With full maturity at end of third day, the colors suffuse to bright magenta Red-Purple Group 67B. Further aging: No further change. Petal texture: Medium, satiny to the touch. Petal number: Commonly approximately 9 to 16 average under normal conditions. Length: 4.5 cm to 5 cm. Width: 4.5 cm. Shape: Obovate. Margin: Entire. Apex: Obcordate. Base: Cuneate. Form: Cupped. Arrangement: Imbricated. Petaloid: Typically none. Persistence: Excellent, petals drop off cleanly before drying. Lastingness: On the plant 4 to 5 days. Cut Flower: 3 days.

*Male reproductive organs*.—Stamens: Number per flower approximately 50 to 80. Anthers: Size: Length: 1 mm; width 1 mm. Arrangement: Regular around styles. Filament: Size: Length: 6-8 mm; width: 0.25 mm. Color: Red Group 49D.

*Pollen*.—Color: Yellow Group 9C.

*Female reproductive organs*.—Pistils: Number per flower: Average of 30. Styles: Color: Yellow-Green Group 154D; Length: 5 mm.

*Stigmas*.—Color: Yellow-Green Group 154D. Length: 0.25 mm.

*Ovary*.—Color: Immature ovary: Yellow-Green Group 154D.

*Mature hips*.—Recurrent from August through October. Color: Red Group 42C. Shape: Rounded to slightly elliptical, medium. Size: 14 mm to 16 mm wide; 13 mm to 15 mm long. Achenes (ripe): Color: Yellow-Green Group 150D. Typically there are 15-20 achenes (which are single seeded fruits) per hip. Shape: Irregular. Length: 4-5 mm. Width: 2-3 mm.

Plant:

*Foliage*.—Compound leaves: Odd pinnate; average of 17 cm in length and 11 cm in width, internode length is an average of 2 cm. Number of leaflets on normal mid-stem leaf: 7 to 9. Quantity. Abundant.

*Color*.—New foliage: Upper Surface: Green Group 137B. Lower surface: Green Group 137D. Leaflets: Size of terminal leaflets: medium (6 cm long and 3.2 cm wide). Non-terminal leaflets: medium (4 cm long and 2.5 cm wide). Shape: Oval. Base shape: Obtuse.

Apex shape: Acute. Texture: glossy, rugose. Edge: Serrated. Serration: Single and small. Color: New foliage of upper surface: Green Group 137B. New foliage of lower surface: Green Group 137D. Old foliage of upper surface: Green Group 137A. Old foliage of lower surface: Green Group 137D. Vein color: New Foliage: Green Group 137B. Old Foliage: Green Group 137A. Venation pattern of leaflets: Pinnate reticulate.

*Petiole*.—Color: Green Group 137A.

*Petiole rachis*.—Color: Green Group 137B. Typical length: 11.5 cm and diameter 2 mm. Texture: Upper surface: smooth, semi-glossy; Lower surface: rough with small prickles.

*Stipules*.—Number: 1 pair. Long and narrow with auricle facing outward, (average of 3.5 cm in length and 1 cm in width). Adnate to petiole, with leafy tips on apex (6 mm length and 3 mm wide), serrated; bearded tip. Color: Upper surface is Green Group 138B on margins, Green Group 138C near center and Green Group 138D on middle ridge. Color: Lower surface is Green Group 138B on margins, Green Group 138C in center. Texture: Upper surface glabrous; lower surface pubescent. Disease resistance: resistance to powdery mildew, blackspot, downy mildew, and rust under normal growing conditions in Burnsville, Minn., U.S.A. and Shreveport, La., U.S.A. Pest Resistance: Not observed.

*Hardiness*.—U.S.D.A. Zone 3-10.

*Drought and heat tolerance*.—Good adaptability in U.S.D.A. Zone 8, Shreveport, La., U.S.A.

*Growth*.—Bushy; very vigorous, upright, and branching.

*Age at maturity*.—3 years. Size: Mature plant: height is 120 cm and width 90 cm. Canes: Heavy caliper, about 1.5-1.8 cm in width, at widest point.

*Rootstock*.—Own root.

*Wood*.—Major Stems: Color: Young, Yellow-Green Group 147D. Mature, Yellow-Green Group 147C. Bark: Young and mature, smooth. Length: 80-90 cm. Diameter: 7-10 mm. Large prickles: Quantity: On major stem from base 35-40 per 15 cm. Form: Long, straight to slightly upward. Length: 5-7 mm. Texture: Soft. Color: Young, Yellow-Green Group 147D. Mature, Greyed-Orange Group 166B. Small Prickles: Quantity: 100-120 per 15 cm. Form: Short, straight. Length: 1-3 mm. Texture: Soft, hairy. Color: Young, Yellow-Green Group 147D. Mature, Greyed-Orange Group 166B. Branches: Color: Young, Yellow-Green Group 147D. Mature, Yellow-Green Group 147C. Length: 25-30 cm. Diameter: 4-5 mm. Internode length: 2.5 cm. Large Prickles: Quantity: On branch from base 25-35 per 15 cm. Form: Long, straight to slightly upward. Length: 3-4 mm. Texture: Soft. Color: Young, Yellow-Green Group 147D. Small Prickles: Quantity: 60-70 per 15 cm. Form: Short, straight to slightly upward. Length: 1-2 mm. Texture: Soft, hairy. Color: Young, Yellow-Green Group 147D. Mature, Greyed-Orange Group 166B.

OTHER CHARACTERISTICS OF THE CULTIVAR DURING WINTER DORMANCY

My observations in U.S.D.A. Zone 4 indicate that the cultivar has ornamental appeal in the winter landscape: Color: Mature hips, Red Group 42B. Color: Leaf foliage, Fall: Yellow Group 7A; Early winter: Grayed-Orange Group 171B. Color: Mature bark, Yellow-Green Group 148C.

I claim:

1. A new and distinct cultivar of Hybrid Rugosa rose plant named 'BOC rogosnif' as herein illustrated and described, characterized particularly as to novelty by the unique flower color combination of beetroot purple and suffused magenta; white streaked eye; prominent gold stamens; strong, cinnamon fragrance; continuous flowering; vigorous growth; resistant to major fungal diseases; readily propagated via budding or rooted cuttings.

* * * * *